(12) United States Patent
Atanasoska et al.

(10) Patent No.: US 8,761,877 B2
(45) Date of Patent: Jun. 24, 2014

(54) BIOSORBABLE BATTERY AND RELATED METHODS

(75) Inventors: Ljiljana Liliana Atanasoska, Edina, MN (US); Michael J. Root, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 654 days.

(21) Appl. No.: 12/572,191

(22) Filed: Oct. 1, 2009

(65) Prior Publication Data

US 2010/0087885 A1 Apr. 8, 2010

Related U.S. Application Data (60) Provisional application No. 61/102,598, filed on Oct. 3, 2008.

(51) Int. Cl.
*A61N 1/00* (2006.01)

(52) U.S. Cl.
USPC ............................................................ 607/9

(58) Field of Classification Search
USPC .................................. 607/9, 35, 75
See application file for complete search history.

(56) References Cited

U.S. PATENT DOCUMENTS

| | | | |
|---|---|---|---|
| 3,708,344 A | 1/1973 | Bernstein | |
| 4,562,841 A | 1/1986 | Brockway et al. | |
| 2004/0073155 A1* | 4/2004 | Laufer et al. | 604/8 |
| 2004/0219428 A1 | 11/2004 | Nagayama | |
| 2004/0234862 A1 | 11/2004 | Macglashan et al. | |
| 2006/0093923 A1* | 5/2006 | Howard et al. | 429/322 |

FOREIGN PATENT DOCUMENTS

| | | |
|---|---|---|
| EP | 1309018 A2 | 5/2003 |
| JP | 2003217601 | 7/2003 |
| JP | 2004335167 | 11/2004 |
| WO | 0110314 | 2/2001 |
| WO | WO-2007/090232 | 8/2007 |

(Continued)

OTHER PUBLICATIONS

"Amended Claims Filed with JPO", in response to JP Office Action dated Apr. 18, 2013 for Japanese Application No. 2011-530272 and corresponding to U.S. Appl. No. 12/572,191, filed with the JPO on Jul. 22, 2013 (3 pages).

(Continued)

*Primary Examiner* — Christopher D Koharski
*Assistant Examiner* — Nadia Ahmad
(74) *Attorney, Agent, or Firm* — Pauley Devries Smith & Deffner, LLC.

(57) ABSTRACT

Embodiments of the invention are related to biosorbable batteries, amongst other things. In an embodiment, the invention includes a biosorbable battery assembly including an anode, a cathode, and a biosorbable separation element. The anode can include an anode material, wherein electrochemical oxidation of the anode material results in the formation of reaction products that are substantially non-toxic. The cathode can include a cathode material, wherein electrochemical reduction of the cathode material results in the formation of reaction products that are substantially non-toxic, the cathode material having a larger standard reduction potential than the material of the anode. The biosorbable separation element can be disposed between the anode and the cathode and can be configured to provide electrical insulation between the anode and the cathode. In an embodiment, the invention includes a medical device system including an implanted medical device and a biosorbable battery in electrical communication with the implanted medical device. Other embodiments are also included herein.

17 Claims, 6 Drawing Sheets

(56) References Cited

FOREIGN PATENT DOCUMENTS

| WO | 2007139668 | 12/2007 |
|---|---|---|
| WO | WO-2008/085904 | 7/2008 |
| WO | 2010040065 | 4/2010 |
| WO | WO-2010/040065 A1 | 4/2010 |

OTHER PUBLICATIONS

"First Office Action", for Japanese Application No. 2011-530272, mailed Apr. 23, 2013 (5 pages).
"International Search Report and Written Opinion from International Application No. PCT/US2009/059397, corresponding to U.S. Appl. No. 12/572,191, mailed Dec. 28, 2009 (13 pages)".
Cho, Yung-Da "Surface treatment of zinc anodes to improve discharge capacity and suppress hydrogen gas evolution", *Journal of Power Sources* 2008, 184: 610-616.
Ciric-Marjanovic, G. "Charge-discharge characteristics of polythiophene as a cathode active material in a rechargeable battery", *Journal of Applied Electrochemistry* 1998, 28: 103-106.
Fonseca, Carla P. "Development of a biodegradable polymer electrolyte for rechargeable batteries.", *Journal of Power Sources* 2006, 155: 381-384.
Fontenier, G. "Long-term in vivo behavior of a platinum endoauricular-magnesium hybrid battery (Abstract only)", *Med. Instrum.* Jul.-Aug. 1975, 9(4):171-176.
Ghanbari, Khadijeh "Synthesis of polyaniline/graphite composite as a cathode of Zn-polyaniline rechargeable battery", *Journal of Power Sources* 2007, 170: 513-519.
Goodenough, John B. "Cathode materials: A personal perspective", *Journal of Power Sources* 2007, 174: 996-1000.
Heublein, B. "Biocorrosion of magnesium alloys: a new principle in cardiovascular implant technology?", *Heart* 2003, 89: 651-656.
Huang, H. "Preparation and electrochemical properties of ZnO/conductive-ceramic nanocomposite as anode material for Ni/Zn rechargeable battery", *Journal of Power Sources* 2008, 184: 663-667.
Jiang, Naixiong "ECS: Bioelectic Battery and Its Applications (Abstract only)", *WorkIt.com* Speaker for December meeting of the San Francisco Bay section of the Electrochemical Society Dec. 13, 2007, 1.
Kirk, R.C. "High Capacity Magnesium Dry Cells", *Journal of the Electrochemical Society* Aug. 1952, pp. 323-327.
Komaba, Shinichi "Enhanced supercapacitive behaviors of birnessite", *Electrochemistry Communications* 2008, 10: 1435-1437.
Lavela, P. "CoFe2O4 and NiFe2O4 synthesized by sol-gel procedures for their use as anode materials for Li ion batteries", *Journal of Power Sources* 2007, 172: 379-387.
Lee, Seo Hwan "Electrochemical properties of new organic radical materials for lithium secondary batteries", *Journal of Power Sources* 2008, 184: 503-507.
Lee, Chris "Scientists create paper-thin, flexible, biodegradable battery", http://arstechnica.com/old/content/2007/08/scientists-create-paper-thin-flexible-biodegradable-battery.ars Aug. 13, 2007, pp. 1-2.
Lee, K.-S. "Synthesis and electrochemical properties of spherical spinel Li1.05M0.05Mn1.9O4 (M=Mg and Al) as a cathode material for lithium-ion batteries by co-precipitation method", *Journal of Power Sources* 2007, 174: 726-729.
Liu, Xiao-Hong "Electrochemical properties of rechargeable aqueous lithium ion batteries with an olivine-type cathode and a Nasicon-type anode", *Journal of Power Sources* doi:10.1016/j.jpowsour.2008.08.050 2007, pp. 1-22.
Manuel, James "Surface-modified maghemite as the cathode material for lithium batteries", *Journal of Power Sources* 2008, 184: 527-531.
Masset, Patrick J. "Thermal activated ("thermal") battery technology Part IIIb. Sulfur and oxide-based cathode materials", *Journal of Power Sources* 2008, 178: 456-466.
Min, Hong-Seok "Fabrication and properties of a carbon/polypyrrole three-dimensional microbattery", *Journal of Power Sources* 2008, 178: 795-800.
Molenda, J. "Electrical conductivity and reaction with lithium of LiFe1—yMnyPO4 olivine-type cathode materials", *Journal of Power Sources* 2007, 174: 689-694.
Nakayama, Masaharu "Electrochemical synthesis of birnessite-type layered manganese oxides for rechargeable lithium batteries", *Journal of Power Sources* 2008, 179: 361-366.
Novak, Petr "Magnesium insertion electrodes for rechargeable nonaqueous batteries—a competitive alternative to lithium?", *Electrochimica Acta* 1999, pp. 351-367.
Nuli, Yanna "A new class of cathode materials for rechargeable magnesium batteries: Organosulfur compounds based on sulfur—sulfur bounds", *Electrochemistry Communications* 2007, 9: 1913-1917.
Richard, Monique "The Behaviour of Lithium and Sodium Iron Oxides as Cathode Materials for Lithium Batteries", *A Thesis Submitted in Partial Fulfillment of the Requirements for the Degree of Master of Science in the Department of Physics*, Simon Fraser University Jun. 1996, pp. 1-97.
Richardson, Thomas J. "Solid solution lithium alloy cermet anodes", *Journal of Power Sources* 2007, 174: 810-812.
Roberts, G. A. "Magnesium silicide as a negative electrode material for lithium-ion batteries", *Journal of Power Sciences* 2002, 110: 424-429.
Teixidor, Genis T. "Fabrication and characterization of three-dimensional carbon electrodes for lithium-ion batteries", *Journal of Power Sources* 2008, 184: 730-740.
Thirunakaran, R. "Performance characteristics of organic-inorganic composite electrodes in magnesium reserve batteries", *Journal of Applied Electrochemistry* 2005, 35:1141-1144.
Wang, L. "Electrospinning synthesis of C/Fe3)4 composite nanofibers and their application for high performance lithium-ion batteries", *Journal of Power Sources* 2008, 184: 717-723.
Whitacre, J. F. "Dual active material composite cathode structures for Li-ion batteries", *Journal of Power Sources* 2008, 177: 528-536.
Winther-Jensen, B. "Control of magnesium interfacial reactions in aqueous electrolytes towards a biocompatible battery", *Electrochimica Acta* 2008, 53: 5881-38.
Witte, F. "In vitro and in vivo corrosion measurements of magnesium alloys", *Biomaterials* 2006, 27: 1013-1018.
Witte, F. "In vivo corrosion of four magnesium alloys and the associated bone response", *Biomaterials* 2005, 26: 3557-3563.
Yang, Yanyan "Nanocrystalline ZnMn2O4 as a novel lithium-storage material", *Electrochemistry Communications* 2008, 10: 1117-1120.

\* cited by examiner

BIOSORBABLE BATTERY AND RELATED METHODS

This application claims the benefit of U.S. Provisional Application No. 61/102,598, filed Oct. 3, 2008, the contents of which are herein incorporated by reference.

TECHNICAL FIELD

This disclosure relates generally to batteries and, more particularly, to batteries that are biosorbable when implanted in a subject, amongst other things.

BACKGROUND OF THE INVENTION

Many types of medical devices are designed to be implanted within the human body. Examples include stents, scaffolds, drug delivery devices, cardiac rhythm management devices, neurological stimulation devices, and the like.

Some implantable medical devices are designed to function by utilizing energy from a power source. Frequently, such devices include a battery, which is implanted into the body as part of the medical device and is typically housed within a sealed case. In many circumstances, the sealed case is made from a relatively noble metal such as titanium to prevent the exposure of the contents of the battery to the in vivo environment.

In the absence of recharging, batteries can only provide a finite amount of power before they are discharged to the point of being useless. In circumstances where a battery has been completely discharged, the battery and the associated medical device must generally be explanted and replaced by a new one, unless the battery was only intended for temporary use. For example, when the battery inside a pacemaker no longer provides sufficient power, the pacemaker must generally be surgically removed and replaced with a new pacemaker.

Unfortunately, removal of implanted devices is not always an easy task. The body's immunological response to a foreign body generally results over time in the formation of fibrous tissue around an implanted medical device. This fibrous tissue can make it difficult to remove implanted medical devices without risking harm to the patient.

SUMMARY OF THE INVENTION

Embodiments of the invention are related to biosorbable batteries, amongst other things. In an embodiment, the invention includes a biosorbable battery assembly including an anode, a cathode, and a biosorbable separation element. The anode can include an anode material, wherein electrochemical oxidation of the anode material results in the formation of reaction products that are substantially non-toxic. The cathode can include a cathode material, wherein electrochemical reduction of the cathode material results in the formation of reaction products that are substantially non-toxic, the cathode material having a larger standard reduction potential than the anode material. The biosorbable separation element can be disposed between the anode and the cathode and can be configured to provide electrical insulation between the anode and the cathode.

In an embodiment, the invention includes a medical device system including an implanted medical device and a biosorbable battery assembly in electrical communication with the implanted medical device. The biosorbable battery assembly can include an anode comprising an anode material, wherein electrochemical oxidation of the anode material results in the formation of reaction products that are substantially non-toxic; a cathode comprising a cathode material, wherein electrochemical reduction of the cathode material results in the formation of reaction products that are substantially non-toxic, the cathode material having a larger standard reduction potential than the anode material; and a biosorbable separation element disposed between the anode and the cathode, configured to provide electrical insulation between the anode and the cathode.

In an embodiment, the invention includes a method of making a biosorbable battery assembly. The method can include coupling an anode to a biosorbable separation element, the anode comprising a first material, wherein electrochemical oxidation of the first material results in the formation of reaction products that are substantially non-toxic, the biosorbable separation element comprising a biosorbable material. The method can also include coupling a cathode to the biosorbable separation element, the cathode comprising a second material, wherein electrochemical reduction of the second material results in the formation of reaction products that are substantially non-toxic, the second material having a larger standard reduction potential than the first material.

In an embodiment, the invention includes a method of using a biosorbable battery assembly. The method can include implanting a biosorbable battery assembly into a subject, the biosorbable battery assembly in electrical communication with a medical device. The biosorbable battery assembly can include an anode, a cathode, and a biosorbable separation element. The anode can include an anode material, wherein electrochemical oxidation of the anode material results in the formation of reaction products that are substantially non-toxic. The cathode can include a cathode material, wherein electrochemical reduction of the cathode material results in the formation of reaction products that are substantially non-toxic, the cathode material having a larger standard reduction potential than the material of the anode. The biosorbable separation element can be disposed between the anode and the cathode and can be configured to provide electrical insulation between the anode and the cathode.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Challenges associated with removing components of an implanted medical device can be obviated by making the implanted device biosorbable. However, in the context of implanted medical devices that require a power source, an additional challenge is presented because existing batteries generally include components that are not biosorbable.

As described herein, embodiments of the present invention include battery assemblies that are biosorbable. Specifically, embodiments herein include batteries with biosorbable components that can harmlessly disintegrate after a period of time within the body. In an embodiment, the invention includes a biosorbable battery assembly including an anode, a cathode, and a biosorbable separation element. The anode can be constructed of a material such that electrochemical oxidation results in the formation of reaction products that are substantially non-toxic. Similarly, the cathode can be constructed of a material such that electrochemical reduction results in the formation of reaction products that are substantially non-toxic. In order to generate a current, the cathode material has a larger standard reduction potential than the material of the anode. Finally, the biosorbable separation element can be disposed between the anode and the cathode. In some embodiments, the biosorbable separation element can be configured to provide electrical insulation between the anode and the cathode, yet permit an electrochemical reaction to occur involving the transfer of ions between the anode and the cathode.

As used herein the term "biosorbable" in reference to a material shall refer to the property of the material being able to be harmlessly absorbed by the body.

As used herein the term "substantially non-toxic" in reference to a chemical compound shall refer to the property of the chemical compound being unlikely to cause harm to an individual at dosages that are reasonably forseeable given the manner in which the chemical compound is being used and/or produced.

Figure 1:
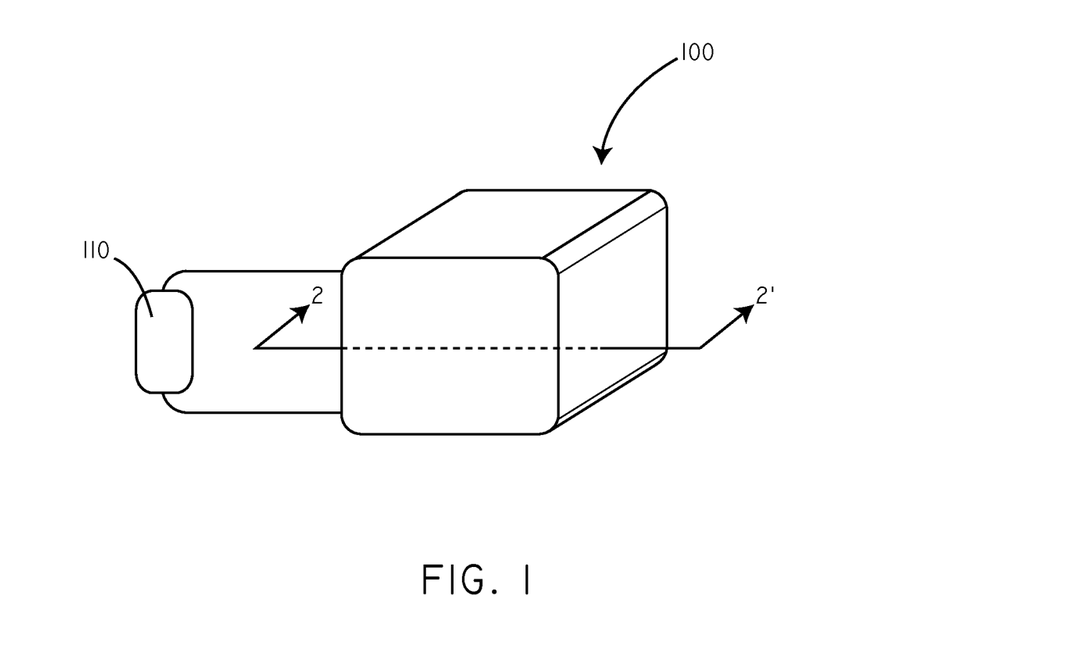
FIG. 1 is a perspective view of a battery assembly in accordance with an embodiment.
Figure 2:
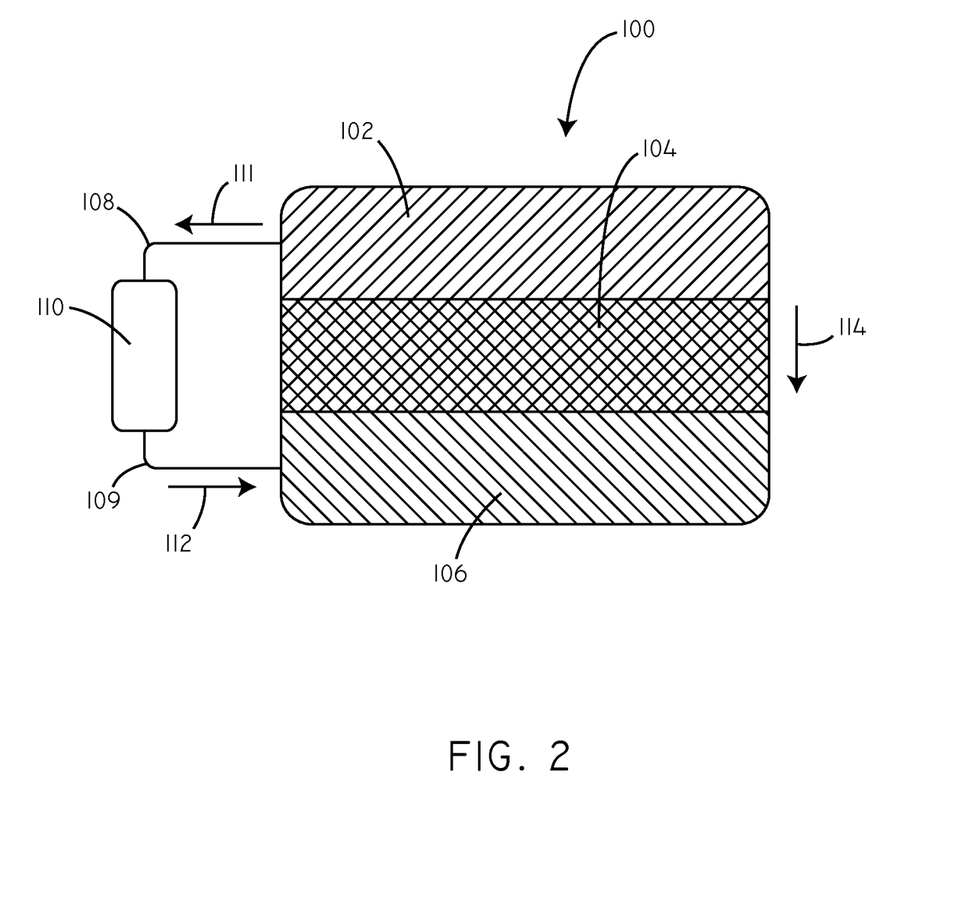
FIG. 2 is a schematic cross-sectional view of a battery assembly as taken along line 2-2' of FIG. 1.

Referring now to FIG. 1, a perspective view of a battery assembly 100 in accordance with an embodiment of the invention is shown in conjunction with a load 110. FIG. 2 shows a cross-sectional schematic view of the battery assembly 100 as taken along line 2-2' of FIG. 1. The battery assembly 100 includes an anode 102, a cathode 106, and a biosorbable separation element 104. The anode 102 can be comprised of a material that, when electrochemically oxidized, breaks down into reaction products that are substantially non-toxic. An extensive discussion of exemplary anode materials is included below. However, for purposes of a specific illustration, in some embodiments the anode 102 can be composed of magnesium. When the magnesium is electrochemically oxidized, magnesium ions are formed and then absorbed into the body.

The cathode 106 can be comprised of a material that when electrochemically reduced breaks down into reaction products that are substantially non-toxic. An extensive discussion of exemplary cathode materials is included below. However, for purposes of a specific illustration, in some embodiments, the cathode 106 can be composed of manganese (IV) oxide. When the manganese (IV) oxide is electrochemically reduced, manganese (III) oxide is formed, which may be further reduced to manganese (II) hydroxide and then absorbed by the body.

The anode 102 is separated from the cathode 106 by the biosorbable separation element 104. The biosorbable separation element 104, in some embodiments, can function to electrically insulate the anode 102 from the cathode 106, so that the electrochemical cell can be made to drive a load 110. In many embodiments, the biosorbable separation element 104 can include electrolytes so as to allow the flow of ions and maintain charge balance during the electrochemical reaction. In some embodiments the biosorbable separation element 104 can include a polymeric matrix. In some embodiments, the polymeric matrix itself can include electrolytes. In some embodiments, an electrolyte composition can be disposed within the polymeric matrix. For example, non-toxic electrolyte salts such as $MgCl_2$ or $NaCl$ can be disposed within the polymeric matrix. In some embodiments, the electrolyte composition can be inserted into the polymeric matrix during manufacturing of the battery assembly 100. In other embodiments, the electrolyte composition, such as a solution including sodium chloride for example, can diffuse into the polymeric matrix after implantation of the battery assembly 100.

In operation, when the battery 100 is activated, such as in various ways described below, it can generate a current to be delivered to a load 110. Specifically, electrons can flow from the anode 102 in the direction of arrow 111 through a first conductor 108. The electrons can then pass through the load 110, through a second conductor 109 in the direction of arrow 112, before completing the circuit at the cathode 106. In order to maintain charge balance, positively charged ions can move in the direction of arrow 114, from the anode 102, through the biosorbable separation element 104 or in some cases around the biosorbable separation element 104, and to the cathode 106.

During the discharging process, the anode 102 will dissolve as the anode material is electrochemically oxidized. For example, where the anode material is magnesium, the anode 102 will be broken down according to the following half-cell reaction:

$$Mg \rightarrow Mg^{2+} + 2e^-$$ Eqn. 1

Where the cathode 106 is manganese (IV) oxide, as a specific example, the corresponding half-cell reaction at the cathode is described by the following half-cell reaction:

$$2MnO_2 + H_2O + 2e^- \rightarrow Mn_2O_3 + 2OH^-$$ Eqn. 2

Pairing these two half-cells, the electrochemical reaction would have a standard potential ($E^0$) of over 2.8 V, while operating voltages of about 1.6 V are realized, indicating that the reaction is spontaneous.

As the anode 102 reacts, a soluble species (in this case $Mg^{2+}$) is formed at the anode 102 which simply dissolves into the extracellular fluid of the body. Similarly, in this case, manganese (III) oxide forms at the cathode 106, which can be further reduced to manganese (II) hydroxide and then dissolve in the extracellular fluid of the body. As such, the anode 102 and cathode 106 erode during operation of the battery and in the process a current is generated, until the anode 102 and/or the cathode 106 is completely dissolved, or until the circuit is otherwise opened.

In some embodiments, electrochemical reduction at the cathode 106 forms a chemical species that, while not highly soluble in the aqueous in vivo environment, nonetheless subsequently breaks down chemically and dissolves after the battery 100 is no longer operational. As such, even in these circumstances, the components of the battery are absorbed by the body.

After the battery 100 ceases operation, whatever remaining elements that are present will degrade, for example the first conductor 108, the second conductor 109, and/or the biosorbable separator 104, will degrade, eventually being totally absorbed by the body. In some embodiments, components such as the first conductor 108 and the second conductor 109 can be made of a material that is more noble (degrades less rapidly) than the anode 102, so that it will continue to function until the anode 102 is dissipated, but it will then itself degrade. By way of example, in some embodiments where the anode 102 is magnesium, the first conductor 108 and the second conductor 109 can be made of aluminum or iron.

It will be appreciated that there are many different half-cell reactions which can be utilized in order to create a battery assembly consistent with embodiments herein, wherein the standard reduction potential of the anode material is less than the standard reduction potential of the cathode material and the reactions at both the anode and cathode generate reaction products that are substantially non-toxic. Specific examples of anode and cathode materials are described in greater detail below.

While the battery of FIGS. 1 and 2 illustrate the use of a single cell, it will be appreciated that embodiments herein include batteries with a plurality of cells. By way of example, in some embodiments, a plurality of anode plates, cathodes plates, and biosorbable separation elements can be used in order to create a battery with a plurality of cells.

Figure 3:
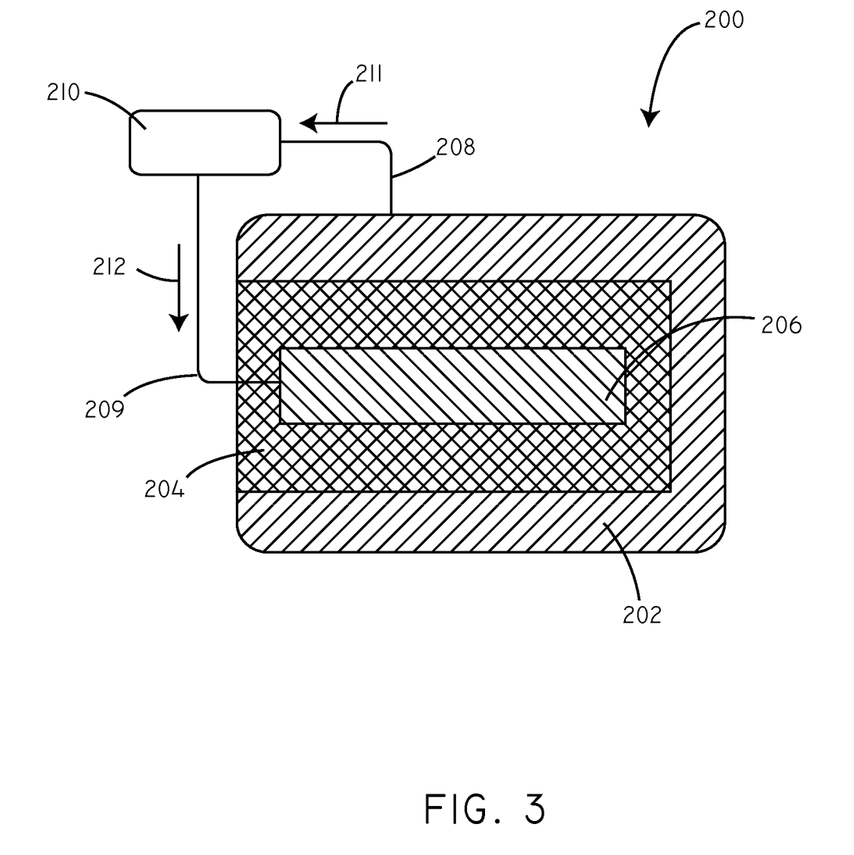
FIG. 3 is a schematic cross-sectional view of a battery assembly in accordance with another embodiment.

Battery assemblies, in accordance with embodiments herein, can take on various physical configurations. By way of example, referring now to FIG. 3, a schematic cross-sectional view of a battery in accordance with another embodiment is shown. In this embodiment, the battery assembly 200 includes an anode 202, a cathode 206, and a biosorbable separation element 204. The anode 202, cathode 206, and biosorbable separation element 204 can be composed of various materials as described more fully below. The battery assembly 200 can further include a first conductor 208 and a second conductor 209, to carry electrons in the direction of arrows 211 and 212 respectively. In operation, the battery assembly 200 can be connected to a load 210. In this embodiment, the biosorbable separation element 204 can surround the cathode 206, with the anode 202 disposed around the outside of the biosorbable separation element.

In some embodiments, battery assemblies in accordance with embodiments herein can include biosorbable coatings disposed on the outside of the battery assembly that degrade after the battery assembly is inserted in vivo. By way of example, the battery assembly can be coated with a biosorbable polymer layer. It is believed that this configuration can be advantageous to protect the battery assembly during the handling steps that may occur prior to implantation and also to increase the structural integrity of the battery assembly. As a specific example, referring now to FIG. 4, the battery assembly 300 can include an anode 302, a biosorbable separator 304, and a cathode 306. The battery assembly 300 can further include a first conductor 308, and a second conductor 309. The battery assembly 300 can be in electrical communication with a load 310. The battery assembly 300 can further include a biosorbable coating 320, disposed around the outside of the battery assembly 300.

Figure 4:
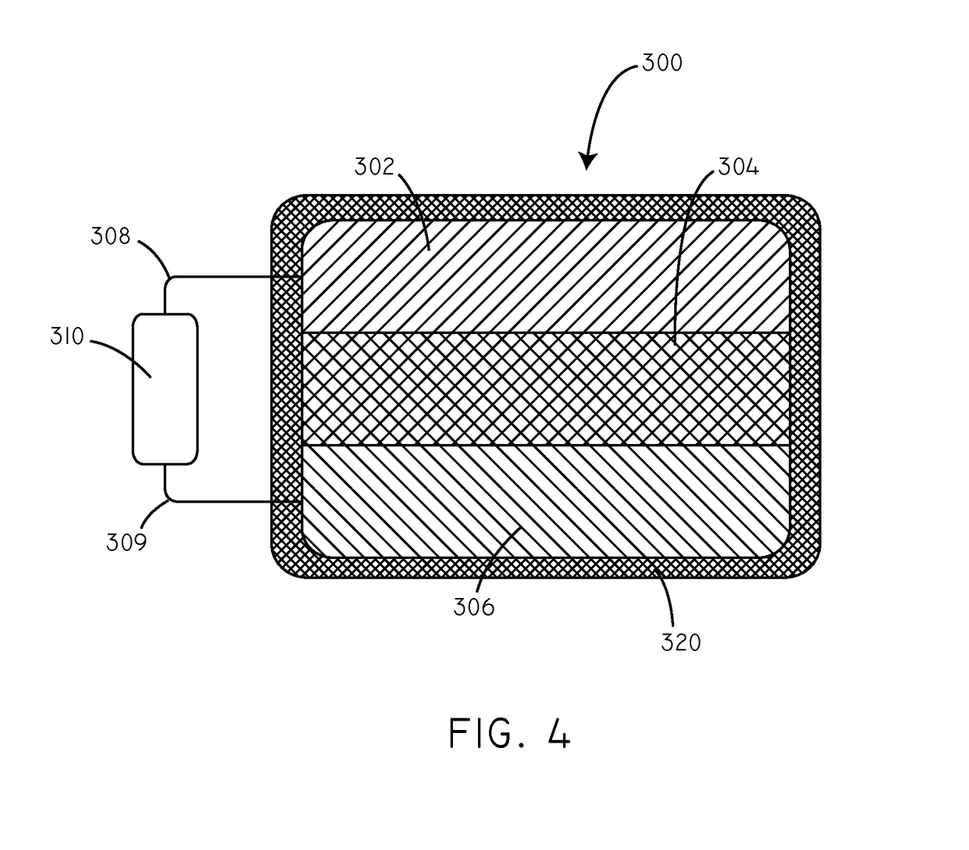
FIG. 4 is a schematic cross-sectional view of a battery assembly in accordance with another embodiment.

The biosorbable coating 320 can be composed of various materials such as biosorbable polymers, carbohydrates, and the like. Biosorbable polymers can include those having hydrolytically labile chemical bonds or bonds that are otherwise subject to enzymatic cleavage. For example, biosorbable polymers can include those having ester, anhydride, or amide bonds in the polymeric backbone. Specific biosorbable polymers can include polylactide (PLA), polyglycolide (PGA), polycaprolactone (PCL), poly(saccharide)s, poly(ethylene oxide), poly(ethylene glycol), copolymers thereof, and the like.

In some embodiments, the biosorbable separation element simply provides electrical insulation between the anode and the cathode. In other embodiments, the biosorbable separation element also provides a conduit for the passage of ions between the anode and the cathode. That is, the battery assembly can be constructed so that the movement of ions needed to maintain charge balance during operation of the battery assembly occurs through the biosorbable separation element, occurs outside of the biosorbable separation element, or occurs through both pathways.

Figure 5:
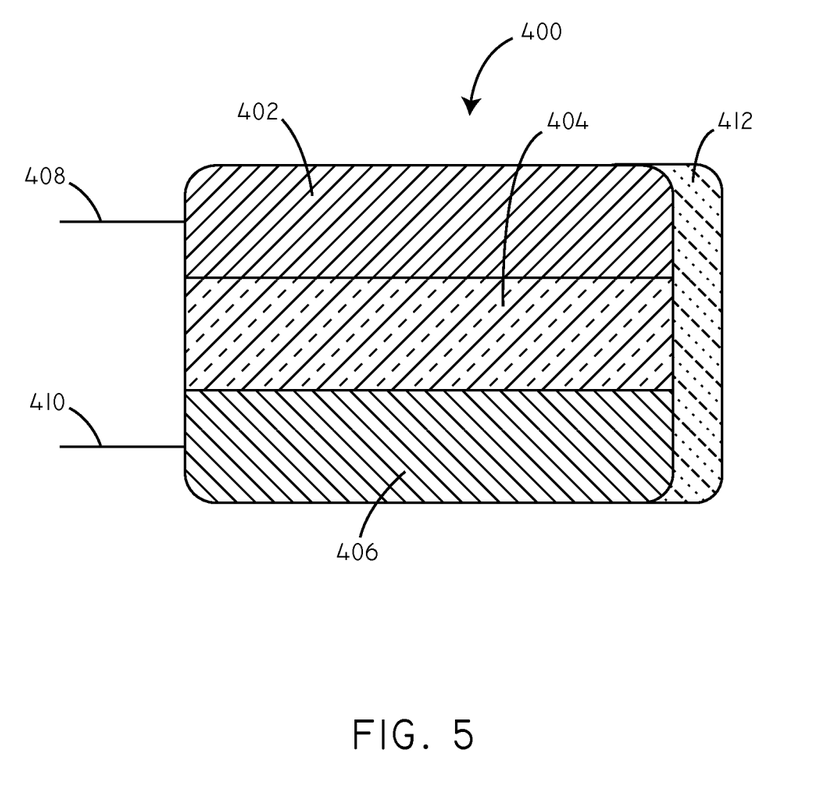
FIG. 5 is a schematic cross-sectional view of a battery assembly in accordance with another embodiment.

Referring now to FIG. 5, a schematic view is shown of a battery assembly wherein the flow of ions occurs through an element other than the biosorbable separator. The battery assembly 400 can include an anode 402, a biosorbable separator 404, a cathode 406, and an ion transfer conduit 412. In this embodiment, the ion transfer conduit 412 can be configured to allow for the transfer of ions between the anode 402 and the cathode 406. Specifically, the ion transfer conduit 412 can include an electrolyte. In some embodiments, the ion transfer conduit 412 can include a porous degradable material, such as a polymer, that can include an electrolyte for purposes of conveying ions. The battery assembly 400 can further include a first conductor 408, and a second conductor 410.

It will be appreciated that in some embodiments the tissue of the body itself can be utilized for the purpose of transferring ions between the anode and the cathode. For example, the extracellular fluid in vivo is an aqueous solution that includes at least some amount of electrolytes such as sodium and potassium. Therefore, extracellular fluid can be used to transfer ions between the anode and the cathode in some embodiments.

Anode Materials

As described above, in operation an electrochemical oxidation reaction takes place at the anode liberating electrons that can then be used to drive a load. The anode material can be selected so that the reaction products of the electrochemical oxidation are substantially non-toxic. In this manner, the reaction products at the anode can simply be absorbed by the body.

It will be appreciated that the anode can be made of many different materials. By way of example, the anode can be made of various metals, various alloys of metals, compounds including metal atoms, ceramic/metal composite and various polymers. Exemplary metals can include calcium, magnesium, iron, bismuth, zinc, and aluminum. In some embodiments, the anode can specifically include magnesium, magnesium alloys, iron, and iron alloys. While not intending to be bound by theory, magnesium and iron can be advantageous as they are both required nutrients and are very safe at the concentrations that would be likely to be achieved by embodiments as disclosed herein. Exemplary polymers can include electrochemically oxidizable degradable polymers, such as various types of organometallic polymers. Other anode materials can include PPy based positive electrode array, carbon MEMS, FeOx-C nanofibers, $(LiTi_2(PO_4)_3)$, ZnO with conductive ceramics such as $Mg(OH)_2$ and $Ca(OH)_2$ nanocomposites, $CoFe_2O_4$.

Cathode Materials

Cathode materials used with embodiments herein can be selected so that electrochemical reduction of the cathode material results in reaction products that are substantially non-toxic.

In some embodiments, the cathode material can include materials such as metal oxides, metal hydroxides, metal oxyhydroxides, polyoxymetallates, metal salts, electrochemically reducible organic compounds, and electrochemically reducible biosorbable polymers. Exemplary metal oxides can include $Mn_2O_3$, $MnO_2$, and $Fe_2O_3$. Further examples of metal oxides can include $Bi_2O_3$ and $Bi_2O_4$. Exemplary metal oxyhydroxides can include MnOOH. Exemplary metal salts can include metal halides, metal sulfides, metal sulfates, and/or metal phosphates. Exemplary metal halides can include $FeCl_3$ and the like. For example, metal sulfides can include $FeS_2$, $Bi_2S_3$, and the like. Exemplary metal sulfates can include $FeSO_4$ and $MnSO_4$. Exemplary metal phosphates can include $FePO_4$ and $MnPO_4$. Exemplary electrochemically reducible organic compounds can include electrochemically active biological compounds, including metalloenzymes and metalloproteins like oxidases, peroxidases, catalases, superoxide dismutases, and derivatives of the same. Specific examples may include ferredoxins and cytochrome c oxidase. Exemplary electrochemically reducible organic compounds can further include metal ion containing macrocycle compounds, including, but not limited to, porphyrins, phthalocyanines and tetraazamacrocycles. Exemplary electrochemically reducible biosorbable polymers can include nontoxic conjugated or nonconjugated polymeric disulfide compounds, conjugated or nonconjugated metallopolymers based on non-toxic metal ion complexes, such as ferrocene (including polyvinylferrocene), Schiff bases or heterocycle metal ion complexes, including, but not limited to, polymeric metal ion heterocycles and metal containing macrocycle compounds like porphyrins, phthalocyanines and tetraazamacrocycles. Exemplary electrochemically reducible biosorbable polymers can also include conjugated organic polymers like polypyrroles, polythiophenes and polyanilines. Exemplary electrochemically reducible biosorbable polymers can also include polymers or copolymers including biosorbable polymer units like polyethylene oxide, polylactide, polycaprolactone or their copolymers. Other cathode materials can include NaFeOx or KFeMnOx; calcium zincate; ZnMnOx; Birnessite type MnOx; iron-manganese phosphate composites; Na or K CoMnCaOx; various organic radical materials; olivine; spherical spinel or spinels in general; PPy/maghemite; and sulfur and oxide based (dual active material composite cathode).

In some embodiments, the cathode material can be a material configured to intercalate ions produced during electrochemical oxidation of the anode. For example, if electrochemical oxidation of the anode material results in the formation of magnesium ions, the cathode material can be selected to be a material that can intercalate magnesium ions. In some embodiments, the cathode material can be a material configured to intercalate other ions, such as sodium and/or hydrogen ions.

Cathode materials used with embodiment herein can be selected so that the cathode material has a higher oxidation potential than the material of the anode. Stated differently, the cathode material can be selected so that is has a larger standard reduction potential than the material of the anode.

Specific pairings of anode and cathode materials include, but are not limited to, those described in Table 1 below.

TABLE 1

| Anode Materials | Cathode Materials |
|---|---|
| Mg | MnOOH |
| Mg | $FePO_4$ |
| Mg | Ferredoxin |
| Mg | Polyethylenedisulfide |
| Fe | FeOOH |

Biosorbable Separation Elements

Various embodiments included herein can include a separation element in order to separate the anode from the cathode. The separation element can be biosorbable in that it can be made of materials that can harmlessly be absorbed by the body, or break-down into chemical species that can harmlessly be absorbed by the body.

It will be appreciated that many different materials can be used in order to create a biosorbable separation element. By way of example, the biosorbable separation element can be made of biosorbable polymers, biosorbable carbohydrates, and the like. Biosorbable polymers can include those having hydrolytically labile chemical bonds or bonds that are otherwise subject to enzymatic cleavage. For example, biosorbable polymers can include those having ester, anhydride, or amide bonds in the polymeric backbone. Specific biosorbable polymers can include polylactide (PLA), polyglycolide (PGA), polycaprolactone (PCL), poly(saccharide)s, poly(ethylene oxide), poly(ethylene glycol), copolymers thereof, and the like. However, it will be appreciated that there are also other biosorbable polymers that can be used and are included within the scope of what is contemplated herein.

In some embodiments, the biosorbable separation element can include a porous polymeric matrix. The porous polymeric matrix can include a biosorbable polymer, such as those described above. In some embodiments, an electrolyte composition can be disposed within the porous polymeric matrix. By way of example, a solution such as a sodium chloride solution, a magnesium chloride solution, or a potassium chloride solution can be disposed within the porous polymeric matrix. In some embodiments, the electrolyte composition can be put within the porous polymeric matrix at the time of manufacturing the battery assembly.

In some embodiments the biosorbable separation element can include a compound that renders the component radio-opaque. By way of example, in some embodiments, the material of the biosorbable separation element can include an x-ray absorbing moiety such as iodine, rendering the biosorbable separation element radio-opaque.

Battery Activation

It will be appreciated that there are various approaches to activating a battery assembly as described herein. By way of example, the battery can be activated through a switching mechanism. That is, a circuit can be closed so that the flow of current is initiated.

In some embodiments, the battery can be activated by diffusion of water and/or electrolytes from the extracellular fluid surrounding the battery structure and into components of the battery assembly. For example, in some embodiments, water and/or electrolytes from the extracellular fluid surrounding the battery can diffuse into the separation element, thus creating a pathway for the migration of ions needed to operate the battery. Specifically, in some embodiments, metal salts such as sodium chloride and the like can be disposed within the porous polymeric matrix, but not in solution, such that the electrolyte is not be immediately active for purposes of transport of ions. In such a case, the battery assembly can be constructed so that water that contacts the outside of the battery assembly, such as after implantation, can diffuse into the porous polymeric matrix, thereby effectively activating the transport of ions.

It will be appreciated that battery devices as described herein can be used in conjunction with many different types of implantable medical devices. Specifically, battery devices as described herein can be used with any type of implantable medical device that requires a power source. Battery devices as described herein can be used in conjunction with both temporary and chronically implanted medical devices. In some embodiments, the invention includes a biosorbable battery in electrical communication with an implantable medical device. Exemplary medical devices can include both biosorbable and non-biosorbable medical devices. Exemplary medical devices can include, but are not limited to, implantable cardiac rhythm management devices (including pacemakers, cardiac resynchronization therapy (CRT) devices, remodeling control therapy (RCT) device, cardioverter/defibrillators, or pacemaker-cardioverter/defibrillators, and the like), neurological stimulators, implantable sensors, and the like. One example of a cardiac rhythm management device is disclosed in commonly assigned U.S. Pat. No. 4,562,841, the content of which is herein incorporated by reference. It will be appreciated that there are also many other examples contemplated.

Figure 6:
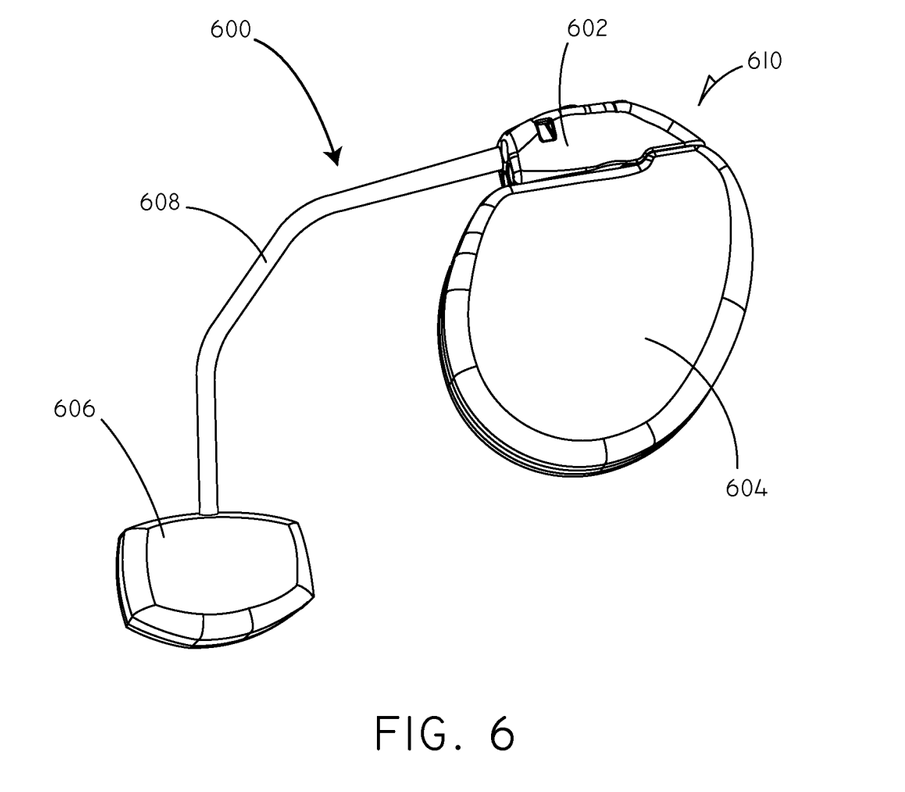
FIG. 6 is a schematic view of a medical device system in accordance with an embodiment.

Referring now to FIG. 6, a schematic view of a medical device system 600 is shown in accordance with an embodiment of the invention. The medical device system 600 includes an implanted medical device 610 and a biosorbable battery 606. A connection lead 608 provided electrical communication between the implanted medical device 610 and the biosorbable battery 606. In this embodiment, the implanted medical device 610 can include a header 602 and a hermetically sealed case 604. Various electrical components including control circuitry are disposed within the case 604. Though not shown in this view, it will be appreciated that the medical device system 600 can also include one or more electrical stimulation leads including electrodes in order to convey electrical stimulation pulses to tissues of the body.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A biosorbable battery assembly comprising:
    an anode comprising an anode material, wherein the anode material is electrochemically oxidized during discharge to release reaction products that are substantially non-toxic and wherein the anode material is configured to dissolve into extracellular fluid of a patient after electrochemical oxidation of the anode material;
    a cathode comprising a cathode material, wherein the cathode material is electrochemically reduced during discharge to form reaction products that are substantially non-toxic and wherein the cathode material is configured to dissolve into extracellular fluid of a patient after electrochemical reduction of the cathode material, the cathode material having a larger standard reduction potential than the anode material; and
    a biosorbable separation element comprising non-toxic electrolytes and a polymeric matrix, the biosorbable separation element disposed between the anode and the cathode and configured to provide electrical insulation between the anode and the cathode.

2. The biosorbable battery assembly of claim 1, the anode material comprising a material selected from the group consisting of magnesium, magnesium alloys, iron, iron alloys, zinc, zinc alloys, aluminum, aluminum alloys, and electrochemically oxidizable degradable polymers.

3. The biosorbable battery assembly of claim 1, the anode material comprising a material selected from the group consisting of magnesium, magnesium alloys, iron, and iron alloys.

4. The biosorbable battery assembly of claim 1, the cathode material comprising a material selected from the group of materials consisting of metal oxides, metal hydroxides, metal oxyhydroxides, polyoxymetallates, metal salts, and electrochemically reducible degradable polymers.

5. The biosorbable battery assembly of claim 4, the metal salts comprising metal halides, metal sulfides, metal sulfates, and/or metal phosphates.

6. The biosorbable battery assembly of claim 1, the cathode material comprising a material selected from the group consisting of $MnOOH$, $Mn_2O_3$, $MnO_2$, and $Fe_2O_3$.

7. The biosorbable battery assembly of claim 1, the cathode material comprising a material configured to intercalate metal ions produced during electrochemical oxidation of the anode.

8. The biosorbable battery assembly of claim 1, the cathode material comprising a material configured to intercalate magnesium, sodium, and/or hydrogen ions.

9. The biosorbable battery assembly of claim 1, the polymeric matrix comprising a polymer selected from the group consisting of polyethylene oxide, polylactide, polycaprolactone, and co-polymers thereof.

10. The biosorbable battery assembly of claim 1, the biosorbable separation element configured to permit the transfer of ions there through, between the anode and the cathode.

11. The biosorbable battery assembly of claim 1, the biosorbable separation element comprising a non-toxic electrolyte solution disposed within the polymeric matrix.

12. The biosorbable battery assembly of claim 1, further comprising a conductor in electrical communication with the anode, the conductor comprising a conductive material more noble than the material of the anode.

13. The biosorbable battery assembly of claim 1, the further comprising a conductor in electrical communication with the cathode, the conductor comprising a conductive material more noble than the material of the anode.

14. A medical device system comprising:

an implanted medical device; and a biosorbable battery assembly in electrical communication with the implanted medical device; the biosorbable battery assembly comprising an anode comprising an anode material, wherein the anode material is electrochemically oxidized during discharge to release reaction products that are substantially non-toxic and wherein the anode material is configured to dissolve into extracellular fluid of a patient after electrochemical oxidation of the anode material;

a cathode comprising a cathode material, wherein the cathode material is electrochemically reduced during discharge to form reaction products that are substantially non-toxic and wherein the cathode material is configured to dissolve into extracellular fluid of a patient after electrochemical reduction of the cathode material, the cathode material having a larger standard reduction potential than the anode material; and a biosorbable separation element comprising a non-toxic electrolyte solution disposed within a polymeric matrix, the biosorbable separation element disposed between the anode and the cathode, configured to provide electrical insulation between the anode and the cathode.

15. The medical device system of claim 14, the implanted medical device comprising a cardiac rhythm management device.

16. The biosorbable battery assembly of claim 1, wherein the anode material is electrochemically oxidized during discharge to release magnesium ions.

17. The biosorbable battery assembly of claim 11, wherein the electrolyte solution comprises $MgCl_2$, NaCl or combinations thereof.

* * * * *